United States Patent [19]

Noh

[11] 4,087,801
[45] May 2, 1978

[54] APPARATUS FOR DETECTING DAMAGES OF CUTTING TOOLS

[75] Inventor: Akihiko Noh, Tokyo, Japan

[73] Assignee: Tokyo Shibaura Electric Co., Ltd., Kawasaki, Japan

[21] Appl. No.: 641,340

[22] Filed: Dec. 16, 1975

[30] Foreign Application Priority Data

| Dec. 20, 1974 | Japan | 49-146452 |
| Apr. 10, 1975 | Japan | 50-43560 |
| Oct. 24, 1975 | Japan | 50-128128 |
| Dec. 20, 1974 | Japan | 49-154893[U] |

[51] Int. Cl.$^2$ ............................................. G08B 21/00
[52] U.S. Cl. .................. 340/267 R; 73/658; 73/104; 340/261
[58] Field of Search .................. 340/261, 267 R, 269; 73/67, 71.4, 104, 67.2, 71.2

[56] References Cited

U.S. PATENT DOCUMENTS

| 3,548,648 | 12/1970 | Weichbrodt et al. | 73/104 |
| 3,793,627 | 2/1974 | Darrel et al. | 340/267 R |
| 3,834,615 | 9/1974 | Watanabe et al. | 235/151.11 |
| 3,841,149 | 10/1974 | Edwin et al. | 73/71.4 |
| 3,913,084 | 10/1975 | Bollinger et al. | 340/261 |
| 3,930,248 | 12/1975 | Keller | 340/267 R |

Primary Examiner—John W. Caldwell, Sr.
Assistant Examiner—Joseph E. Nowicki
Attorney, Agent, or Firm—Finnegan, Henderson, Farabow & Garrett

[57] ABSTRACT

A detector for producing an output corresponding to the vibration of a cutting tool or a workpiece worked thereby, a signal processing circuit for obtaining the root mean square value of the output signal from the detector, and a comparator for comparing the output signal from the signal processing circuit with data produced at the time of normal cutting whereby when an abnormal vibration occurs due to the damage of the cutting tool the cutting operation is stopped by using a signal from the comparator.

4 Claims, 17 Drawing Figures

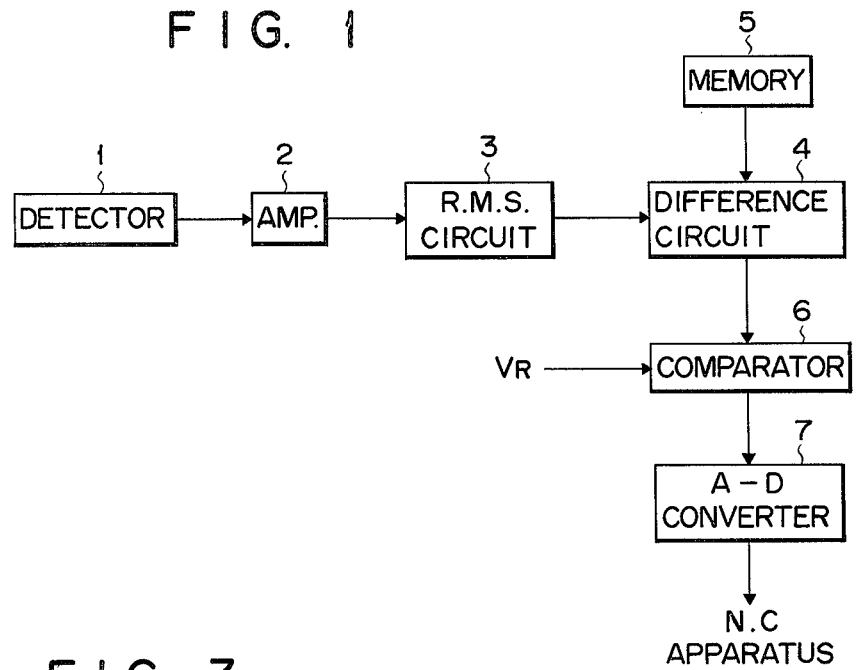
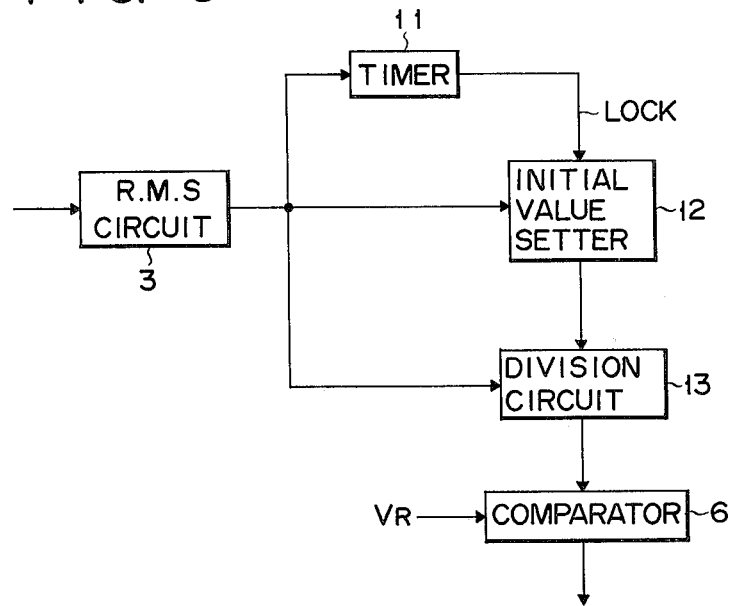

APPARATUS FOR DETECTING DAMAGES OF CUTTING TOOLS

This invention relates to apparatus for detecting damages of cutting tools.

With recent advance of numerical control systems full automatic operations of various machine tools have been used widely. In such machine tools since control signals for a predetermined feed or cut are automatically applied to working tables or tool posts according to prescribed programs, even when the cutting tools are damaged or worn out, the cutting operations are continued thus forming rejects.

Accordingly, it is an object of this invention to provide novel apparatus for immediately detecting the damage of the cutting tool during cutting operation so as to stop the cutting operation thus preventing formation of rejects.

According to this invention there is provided apparatus for detecting a damage of a cutting tool of the type comprising a detector for producing an output corresponding to the vibration of a cutting tool or a workpiece worked thereby, a signal processing circuit for processing the output signal from the detector, a normal data memory circuit for producing an output data signal representing the output from the signal processing circuit under normal cutting conditions, such output being determined at a predetermined period after the commencement of cutting operations, and means for comparing the output from the signal processing circuit with the output data signal, characterized in that the signal processing circuit includes a root mean square circuit for obtaining the root mean square value of the output signal from the detector.

This invention can be more fully understood from the following detailed description when taken in conjunction with the accompanying drawings, in which:

FIG. 1 is a block diagram showing one embodiment of this invention;

FIG. 3 is a block diagram showing a modified embodiment of this invention;

Figure 2A:
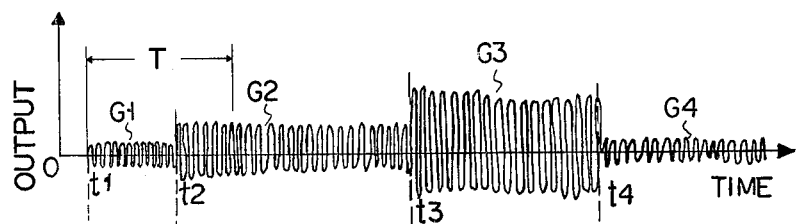
FIGS. 2A through 2F show signal waveforms utilized to explain the operation of the apparatus shown in FIG. 1.

Referring now to FIG. 1, a preferred embodiment of this invention shown therein comprises a detector 1 including a piezoelectric element, for example, and mounted on the working table or tool post of a machine tool for producing an electric signal corresponding to the vibration created on the working table or tool post during the cutting operation. Where a piezoelectric element is used as the detector it produces an electric signal proportional to the acceleration of the mechanical vibration as shown in FIG. 2A, for example. In FIG. 2A, when the machine tool is started at time $t_1$ the detector 1 detects a small vibration of the machine tool caused by the driving motor, for example, thereby producing a first acceleration signal $G_1$. When the cutting operation is commenced at a time $t_2$, the detector 1 will produce a second acceleration signal $G_2$ so long as the cutting tool is normal. When the cutting tool is damaged at a time $t_3$ the detector 1 will produce a third acceleration signal $G_3$ having a large amplitude. Thereafter, the cutting tool is separated from the workpiece at a time $t_4$ whereby abnormal vibration terminates and the detector output decreases to a lower level $G_4$.

Figure 2B:
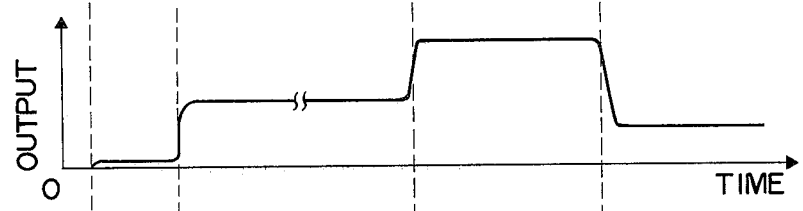

The output signal from the detector 1 is applied to a root mean square (R.M.S.) circuit 3 after being amplified by an amplifier 2, if desired, where the root mean square value of the detector output is obtained. The output from the R.M.S. circuit 3 has a level proportional to the mean values of the levels of respective acceleration signals $G_1$ through $G_4$, as shown in FIG. 2B.

Figure 2C:
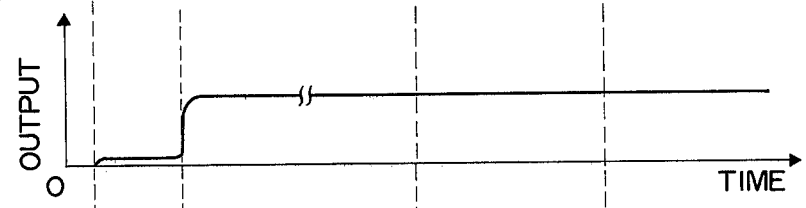

The output from the R.M.S. circuit 3 is applied to one input of a difference circuit 4 with its other input connected to a data memory circuit 5. The data memory circuit includes a data storing medium in the form of a magnetic tape, magnetic drum or a perforated tape for continuously storing the output of the detector 1 starting from the time of commencing the cutting operation by using a normal cutting tool. FIG. 2C shows the output of the detector 1 when a steel rod is cut to a uniform depth by a lathe. The output level of the data memory circuit 5 is substantially the same as the level of the portion of the output shown in FIG. 2B corresponding to the acceleration signal $G_2$.

Figure 2D:
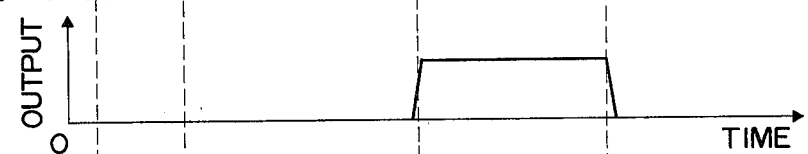
Figure 2E:
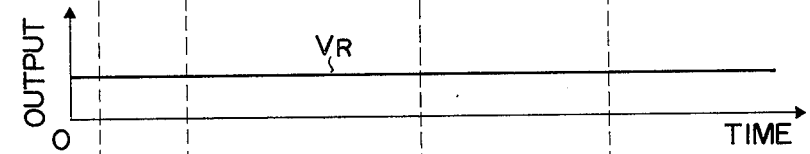
Figure 2F:
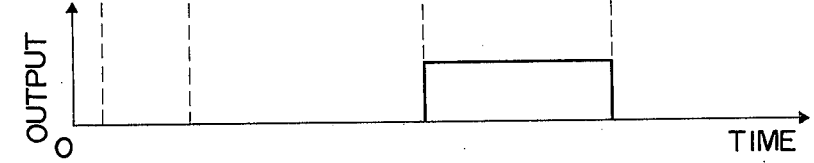

Difference circuit 4 produces a signal for an interval between $t_3$ and $t_4$ as shown in FIG. 2D and having a level corresponding to a difference of the levels of the output from the R.M.S. circuit 3 (FIG. 2B) and the output from the date memory circuit as shown in FIG. 2C. This output from the difference circuit 4 is supplied to one input of a comparator 6 with the other input connected to receive a reference signal VR having a constant level as shown in FIG. 2E. The purpose of the comparator 6 is to operate when the difference in the levels of the normal data and actually measured data increases beyond a predetermined definite value thereby detecting such condition as the damage or deterioration of the cutting tool. Accordingly, the level of the reference signal VR is set to a suitable value for this purpose. The output from the comparator 6 shown in FIG. 2F is applied to a numerical control apparatus of the machine tool via an analogue-digital converter 7. For example, the driving motor of the machine tool is stopped and the tool is separated from the workpiece at the leading edge of the comparator output. In this manner, according to this embodiment when the tool is damaged at the time $t_3$ the cutting operation is immediately stopped thus preventing formation of rejects.

Although in the embodiment shown in FIG. 1 the normal data which has been stored in the data memory circuit 5 is compared with the data actually measured by the detector 1, it is also possible to store the actually measured data under normal condition at the commencement of the cutting operation for comparing this initial value with the data measured later. FIG. 3 shows a modified embodiment based on this concept wherein the elements corresponding to those shown in FIG. 1 are designated by the same reference numerals.

In the circuit shown in FIG. 3, the output from the R.M.S. circuit 3 is sent to a timer 11, an initial value setter 12 and a division circuit 13. The timer 11 comprises a delay circuit for locking the output from the initial value setter 12 to the level of the normal acceleration signal $G_2$ shown by FIG. 2A, for example thereby supplying a locking signal to the initial value setter 12 when a time period T elapses after the time point $t_1$ in FIG. 2A, for example. In response to the locking signal, the initial value setter 12 sends an output to the division circuit 13, which output is locked to the level of the input signal from the R.M.S. circuit 3.

Figure 4:
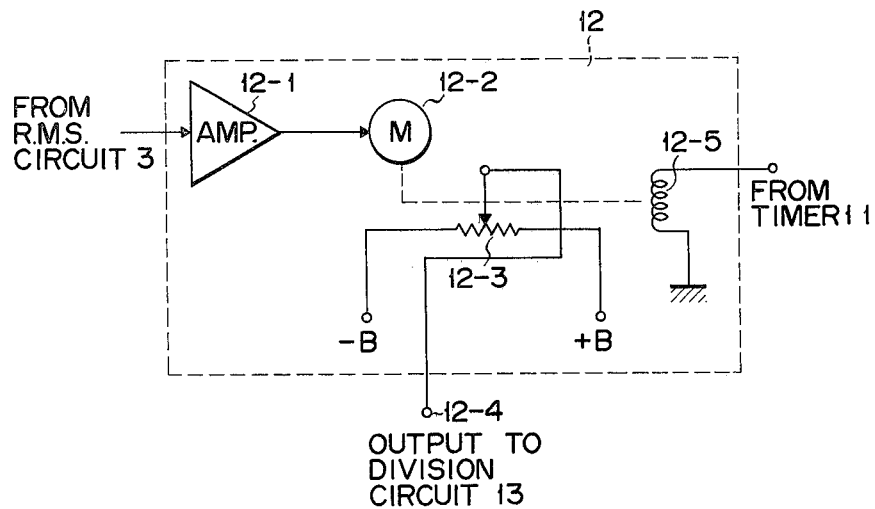
FIG. 4 is a block diagram showing one example of the initial value setter utilized in the apparatus shown in FIG. 3.

Initial value setter 12 having a constructin as shown in FIG. 4 are available in the market. In FIG. 4, the output from the R.M.S. circuit 3 is amplified by an amplifier 12-1 and then applied to a servomotor 12-2 which rotates to an angular position corresponding to the level of the DC current output from the amplifier 12-1. The shaft of the servomotor 12-2 carries a sliding contact of a potentiometer 12-3 connected between sources $+B$ and $-B$ so that an output having a level corresonding to the input signal from the R.M.S. circuit 3 appears on an output terminal 12-4. When a locking signal from the timer 11 is applied to locking winding 12-5, the sliding contact of the potentiometer 12-3 is locked thus preventing the motion in accordance with the rotation of the servomotor 12-2.

The output from the initial value setter 12 which has been locked by the locking signal from the timer 11 in a manner just described is applied to the division circuit 13 together with the output from the R.M.S. circuit 3, whereby the ratio between these two inputs is determined. So long as the cutting tool is normal, these two inputs have substantially the same level so that the division circuit 13 produces an output having an extremly small level. However, when the cutting tool is damaged, the level of the output from the R.M.S. circuit 3 increases greatly with the result that the output from the division circuit 13 also increases greatly. When this output exceeds the reference value $v_R$, the comparator 6 will produce a damage detection signal of the cutting tool in the same manner as has been described in connection with FIG. 1.

In the case of FIG. 1, the cutting ability of the tool at the time of measuring the normal data is not always same to that at the time of actual measurement so that it is necessary to adjust the level (or zero adjustment) each time the measurement is made whereas in the case of FIG. 3 since the same cutting tool is used to obtain the normal data and the measured data, the so called zero adjustment is not necessary.

Figure 5:
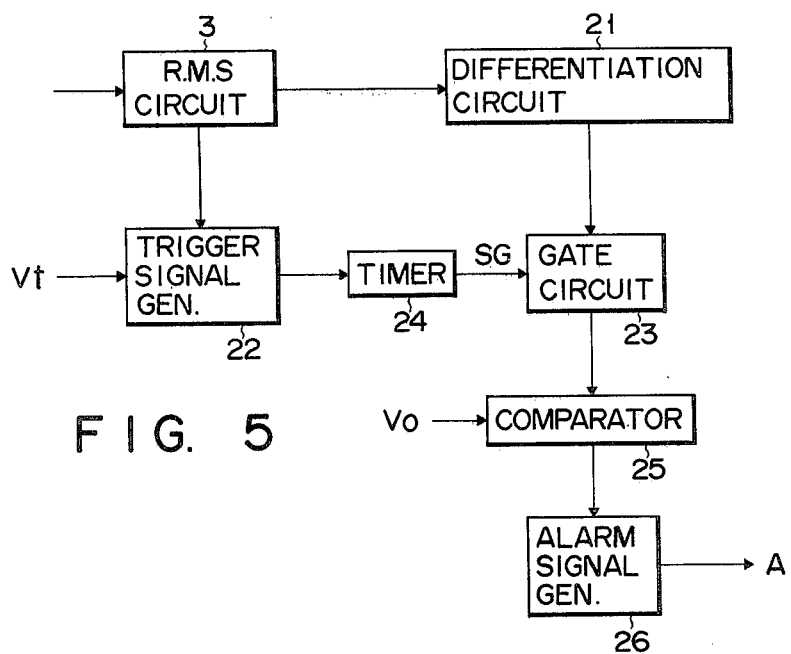
FIG. 5 is a block diagram showing still another embodiment of this invention.

In still another modification of this invention shown in FIG. 5, the output from the R.M.S. circuit 3 is sent to a differentiation circuit 21 and a trigger signal generator 22. The differentiation circuit 21 functions to differentiate the root mean square value applied thereto from the R.M.S. circuit 3 and to apply its output to a gate circuit 23 which is used to pass this output to a comparator 25 in accordance with the output from a timer circuit 24 to be described later in detail. The output from the differentiation circuit 21 passing through the gate circuit 23 is applied to one input of the comparator 25 having the other input connected to receive a normal reference value $v_0$. When the output from the diferentiation circuit 21 exceeds the normal reference value $V_0$, the comparator 25 sends an output to an alarm signal generator 26 for producing an alarm signal A which is used to operate an alarm device (not shown) and or to stop the machine tool.

A trigger reference signal $V_t$ is applied to the other input of the trigger signal generator 22 thus causing the same to send a trigger signal to the timer 24 when the input from the R.M.S. circuit 3 exceeds the reference signal $V_t$. In response to the trigger signal the timer circuit 24 begins its timing operation and when a definite time T has elapsed it applies a gate signal to the gate circuit 23. Thus the trigger signal generator 22 and the timer 24 close the gate circuit 23 for a predetermined interval T following the building up of the output of the R.M.S. circuit 3 for preventing the output from the differentiation circuit 21 from passing through the gate circuit 23 for the interval T.

Figure 6A:
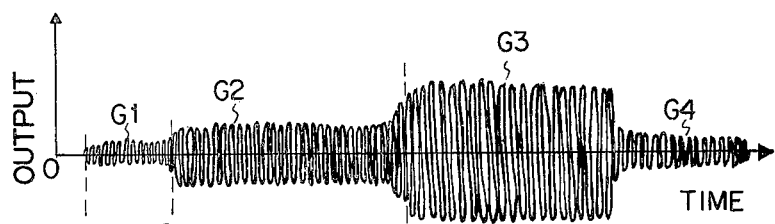
FIGS. 6A through 6G are signal waveforms useful to explain the operation of the apparatus shown in FIG. 5.
Figure 6B:
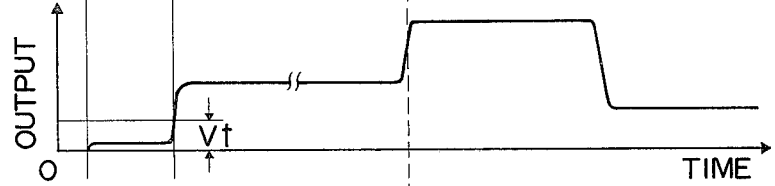
Figure 6C:
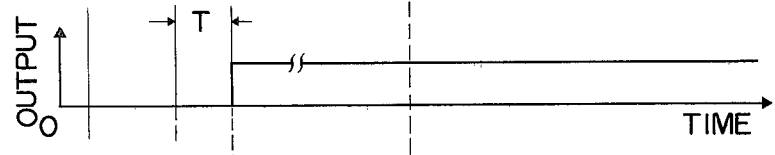
Figure 6D:
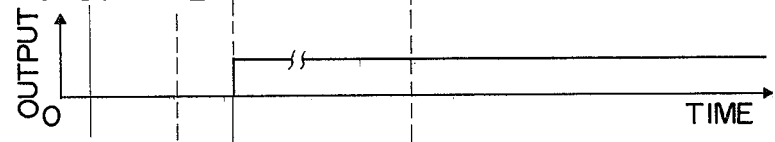
Figure 6E:
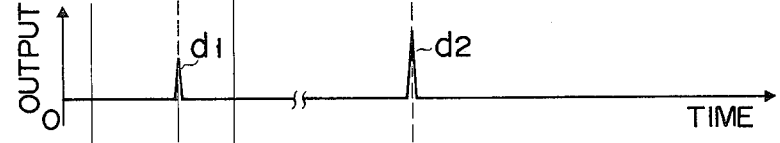

The operation of the modification shown in FIG. 5 will now be described with reference to FIGS. 6A through 6G. FIG. 6A shows the output signal from the detector 1 under the same cutting condition as has been described in connection with FIG. 2A and FIG. 6B shows the output from the R.M.S. circuit 3 like FIG. 2B. When the cutting operation is commenced at a time $t_2$ the output from the R.M.S. circuit 3 comes to exceed the trigger reference value $V_t$ as shown in FIG. 6B whereby the trigger signal generator 22 applies the trigger signal to timer 24. At this time the differentiation circuit 21 produces a differentiated output $d_1$ as shown in FIG. 6E but at this time since the gate circuit 23 is not yet enabled, the signal $d_1$ is not sent to the comparator 25. When the interval T elapses the timer 24 sends a gate signal having a constant level to the gate circuit 23 as shown by FIG. 6C. Thereafter, the gate circuit 23 is maintained in its opened state as shown by FIG. 6D.

Figure 6F:
Figure 6G:
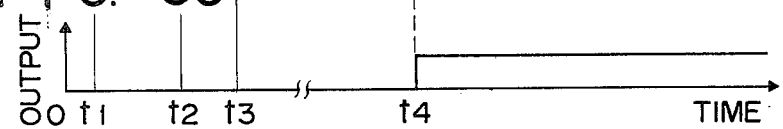

When the cutting tool is damaged at a time $t_4$ the output from the R.M.S. circuit 3 increases abruptly and the differentiating circuit 21 produces an output $d_2$ shown in FIG. 6E in response to the increased output from the R.M.S. circuit 3. An output $d_2$ is applied to one input of the comparator 25 through the gate circuit 23 to be compared with the reference value $V_0$ applied to the other input of the comparator 25. As shown in FIG. 6F, as the peak value of the differentiated output $d_2$ is larger than the reference value $V_0$ the comparator 25 provides a tool damage detection signal to the alarm signal generator 26 thereby producing the alarm signal A at the time $t_4$ as shown in FIG. 6G.

The embodiment shown in FIG. 5 is characterized in that the detection signal produced by the detector and representing the acceleration of vibration is differentiated by the differentiation circuit 21. For this reason, it is possible to quickly detect rapid changes in the detection signal thereby increasing the response speed of the damage detector.

As the working condition differs with the type of the machine tool, the acceleration of vibration also varies widely. However, according to this embodiment since the differentiated value of the root mean square value of the acceleration is detected, the novel detecting device of this invention can be applied to machine tools of any type.

What is claimed is:

1. Apparatus for detecting damage of a cutting tool comprising a detector for producing a detection output signal in accordance with vibration created by at least one of a cutting tool or a workpiece worked thereby during a cutting operation, a signal processing circuit including a root mean square circuit for producing a root mean square signal representing the root mean square value of said detection output signal from said detector, a normal data memory circuit for producing an output data signal at the time of normal cutting, said normal data memory circuit comprising a timer which produces an output signal a predetermined interval after the appearance of said root mean square signal and an initial value setter which produces said output data signal having a value corresponding to the level of said root mean square signal existing at the time when said timer output signal is produced, and comparator means for comparing said output data signal from said normal darta memory circuit with said root mean square signal.

2. The detecting apparatus as claimed in claim 1 wherein said comparator means comprises a division circuit for producing a division output signal representing the ratio between said output data signal and said root mean square signal, and a comparator circuit for comparing said division output signal with a predetermined reference value.

3. The detecting apparatus as claimed in claim 1 wherein said initial value setter comprises an amplifier for amplifying said root mean square signal, a servomotor having an output shaft driven in response to said amplified root mean square signal, a potentiometer having a slide arm moved to a position corresponding to the angular position of said shaft of said servomotor, and means for locking said slide arm in response to said timer output signal.

4. The detecting apparatus as claimed in claim 2, wherein said signal processing circuit includes an amplifier for amplifying said detection output signal.

* * * * *

UNITED STATES PATENT OFFICE
CERTIFICATE OF CORRECTION

Patent No. 4,087,801  Dated May 2, 1978

Inventor(s) Akihiko Noh

It is certified that error appears in the above-identified patent and that said Letters Patent are hereby corrected as shown below:

Column 5,  line 4,  change "darta" to --data--.

Signed and Sealed this

Second Day of January 1979

[SEAL]

Attest:

RUTH C. MASON
Attesting Officer

DONALD W. BANNER
Commissioner of Patents and Trademarks